United States Patent [19]
Goldstein

[11] 4,053,952
[45] Oct. 18, 1977

[54] MAGNETIC FLUID ACTUATED CONTROL VALVE, RELIEF VALVE AND PUMP

[75] Inventor: Seth R. Goldstein, Bethesda, Md.

[73] Assignee: The United States of America as represented by the Secretary of the Department of Health, Education and Welfare, Washington, D.C.

[21] Appl. No.: 786,486

[22] Filed: Apr. 8, 1977

Related U.S. Application Data

[63] Continuation of Ser. No. 621,543, Oct. 10, 1975, abandoned.

[51] Int. Cl.² .......................... A21F 1/24; F04B 43/00
[52] U.S. Cl. ................................................ 3/1.1; 3/1.2; 128/346; 128/DIG. 25; 417/412
[58] Field of Search .................. 3/1, 1.1, 1.2, 1.5, 3/1.7; 128/DIG. 25, 346, 213, 214; 251/4; 417/412, 413

[56] References Cited
U.S. PATENT DOCUMENTS

| 2,743,898 | 5/1956 | King, Jr. ........................... 251/139 |
| 2,930,324 | 3/1960 | Toulmin, Jr. ........................ 3/1.7 X |
| 3,381,623 | 5/1968 | Elliott ................................ 417/413 |
| 3,419,008 | 12/1968 | Plishner ............................ 128/346 |
| 3,496,878 | 2/1970 | Hargem et al. .................... 417/413 |
| 3,511,583 | 5/1970 | Brown ................................ 3/1.7 |
| 3,520,641 | 7/1970 | Casey ................................. 417/412 |
| 3,538,917 | 11/1970 | Selker ............................. 128/DIG. 25 |
| 3,601,124 | 8/1971 | Petree ............................. 128/214 E |
| 3,733,616 | 5/1973 | Willis, Jr. .......................... 3/1.7 |
| 3,784,334 | 1/1974 | Hilgert ............................. 417/413 X |
| 3,817,237 | 6/1974 | Bolduc ............................. 128/346 X |
| 3,939,821 | 2/1976 | Roth ................................ 128/DIG. 25 |

Primary Examiner—Louis G. Mancene
Assistant Examiner—Paul J. Hirsch
Attorney, Agent, or Firm—Browdy and Neimark

[57] ABSTRACT

An electrically controlled magnetic fluid actuated device, which can be used in controlling fluid flow and which has particular utility in controlling this flow from a pressurized reservoir implanted in the body such as might be used for an artificial pancreas, sphincter for bladder control or other orthotic devices in the body of a human, has no freely moving parts and consists of a flow passageway having a portion the cross-section of which may be varied to control and to stop the flow of fluid, such as medicine, from a reservoir in the body to the point where this fluid is needed. A magnetic fluid which surrounds or contacts this portion of the passageway can, according to the presence or lack of a magnetic flux in its vicinity, occlude the passageway or allow it to open so as to control the fluid flow in the flow member.

15 Claims, 2 Drawing Figures

MAGNETIC FLUID ACTUATED CONTROL VALVE, RELIEF VALVE AND PUMP

This is a continuation of application Ser. No. 621,543, filed Oct. 10, 1975 now abandoned.

THE FIELD OF THE INVENTION

This invention relates to the control of fluid flow and, more particularly, to an electrically controlled magnetic fluid actuated device which contains no freely moving parts and which has particular utility as the output element of an artificial pancreas or sphincter or the like for controlling fluid flow from or to different organs in the body of a human.

BACKGROUND OF THE INVENTION

The conventional manner of controlling a fluid flow from an artificial pancreas or other artificial organ in the human body by a remote command would be either to use an electrically actuated moving part valve such as a poppet or spool, etc., or to use a spring loaded solenoid to occlude a tube which is opened when the solenoid is electrically actuated. However, these devices contain moving parts and are subject to wear, and potential malfunction due to jamming, etc. In applications involving human implantation, failure could at worst be lethal, and at the least require surgical removal.

SUMMARY OF THE INVENTION

It is, accordingly, an object of the present invention to overcome the defects of the prior art, as mentioned above.

Another object is to provide for improved and simplified fluid flow from artificial organs in the body of an animal, such as a human.

Another object of the present invention is to provide an electrically controlled magnetic fluid actuated valve which can be implanted in the body of a human.

A further object of the present invention is to provide an electrically controlled valve which is both simple and reliable.

Still another object of the present invention is to provide an electrically controlled valve which contains no freely moving parts.

Yet another object of the present invention is to provide an electrically controlled valve which utilizes a magnetic fluid for actuation.

Yet another object of the present invention is to provide a passive pressure relief valve which allows fluid to pass only if line pressure is higher than a predetermined value.

Yet a further object of the present invention is to provide an electrically controlled magnetic fluid actuated pump capable of delivering minute increments of fluid at a pressure substantially higher than the fluid reservoir pressure.

These and other objects of the invention are fulfilled by a highly reliable and compact "no moving parts" electrically controlled magnetic fluid actuated mechanism, either in valve or pump form, which is suitable for controlling the flow of liquid coming from a pressurized reservoir implanted in the body such as might be used for an artificial pancreas, sphincter for bladder control, or other orthotic device.

The control valve mode comprises a fluid passageway having a variable cross-section portion, such as a thin-walled flexible, e.g. elastomer, tubing or a chamber having an elastic membrane which is used to control the flow of fluid from a pressurized reservoir to a desired location in the body. The variable cross-section portion of the passageway is located within a region of high magnetic field, e.g. between two pole pieces in permanent magnetic circuit. A magnetic fluid is located in this region of high magnetic field and contacts the outside surfaces of the variable cross-section portion. The magnetic fluid has the property that its internal pressure is dependent on the magnetic field inside it. If the magnetic field is sufficiently intense, the pressure exerted by the magnetic fluid is great enough to occlude the passageway. If the magnetic field is reduced, the reduced pressure in the magnetic fluid allows the fluid pressure inside the passageway, i.e. the reservoir pressure, to open up the previously occluded passageway allowing a through flow.

The magnetic field reduction is accomplished either by opposing the existing magnetic field with a second magnetic field produced by an appropriately positioned electromagnet, or by removing or reducing the existing magnetic field. In either case this can be electrically controlled. When minimum power consumption is desired, as would be the case for human implantation, permanent magnets can provide the magnetic field that occludes the tube and the current pulses which reduce the field can be on the order of 10 milliseconds long.

This device is fail-safe in that an electrical power failure results in no flow from the reservoir. Membrane or tube breakage likewise results in no flow since the bolus of the magnetic fluid will stay between the optional pole pieces which adjoin the two permanent magnets or adjacent to the permanent magnets themselves and prevent passage of the liquid.

The relief valve mode is conceptually identical to the above described control valve mode except it does not have the means for reducing the magnetic field from its nominal value, i.e. there is no energy input and no change in the magnetic field. Thus, liquid passes through the passageway past the variable cross-section portion only if the liquid pressure within the passageway exceeds the external pressure produced by the magnetic fluid. Typically, this external pressure is established by a predetermined length of permanent magnet material which provides the desired magnetic field and sets the relief pressure level.

The pump mode of the device comprises the structure of the previously described control valve, the previously described relief valve, a check valve, and a liquid supply reservoir at low pressure. The reservoir is connected to the control valve through a check valve which prevents liquid from going back into the reservoir. The control valve is connected to the liquid delivery point via the pressure relief valve which remains closed unless the liquid pressure in the line exceeds a predetermined level higher than the pressure in the liquid reservoir but lower than the pressure of the control valve.

The flow passage of the control valve is normally occluded by the internal pressure of the magnetic fluid. When this pressure is reduced to a suitably low level by reducing the control valve magnetic field, the flow passage opens and liquid from the reservoir flows into the space generated by the expansion of the cross-section of the variable sized portion of the passageway. But, the reservoir fluid still does not flow through the system to the delivery point because it is stopped by the relief valve. When the magnetic field in the control valve is then increased to its previous value, the flexible flow passage is occluded and the fluid, e.g. medicine, is displaced and flows out to the delivery point since the relief valve "set pressure" is less than the pressure generated by the magnetic fluid.

BRIEF DESCRIPTION OF THE DRAWING

The above and additional objects and advantages of the present invention will become more apparent by reference to the description of illustrated embodiments in a drawing thereof in which.

DETAILED DESCRIPTION OF SPECIFIC EMBODIMENTS

Figure 1:
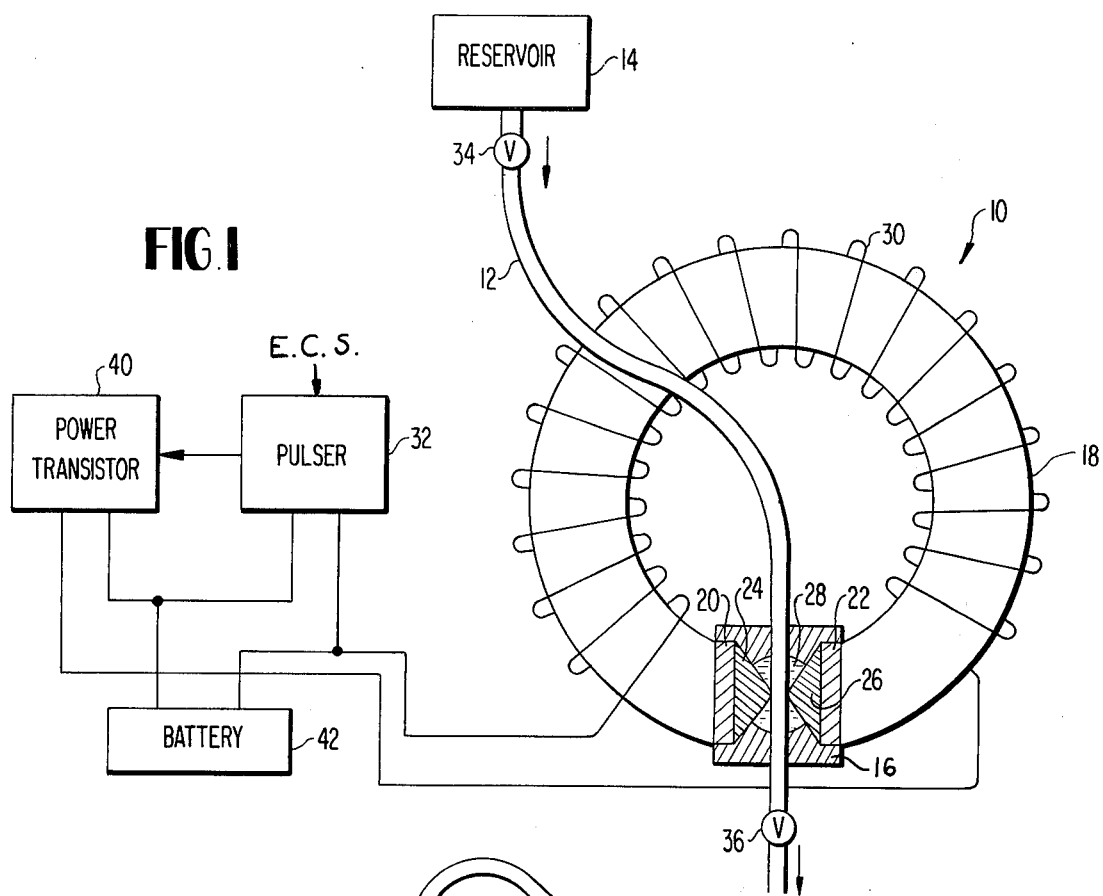
FIG. 1 is a schematic view of one embodiment of the electrically controlled magnetic fluid actuated switch in accordance with the present invention.

FIG. 1 shows one embodiment of a magnetic fluid device 10 which utilizes a flexible thin-walled tubing 12 for the fluid passageway. This tubing 12 is connected at one end to a pressurized reservoir 14 which contains the liquid the delivery of which is to be controlled, and the other end of the tubing 12 extends to the location in the body where such fluid, e.g. medicine, is to be delivered. The device 10 of this invention can be operated either as a controlled on-off valve or as a pump as will be discussed below. In the valve mode, the pressure in the reservoir 14 can be approximately 5 to 10 psi whereas in the pump mode, the pressure can be about 1 psi.

The tubing 12 passes through a housing 16 provided with a hole in the top and the bottom through which the tubing passes. This housing 16 contains a magnetic fluid 28, two permanent magnets 20 and 22, and two optional pole pieces 24 and 26. Each of the permanent magnets is attached to the end of a toroidal-shaped soft iron core 18 which has an electrical coil 30 wrapped around it in the manner schematically shown in FIG. 1. Each of the pole pieces 24 and 26 adjoins one of the permanent magnets 20 or 22 and is typically a truncated cone with the smaller end of the cone directed toward the tubing 12. The pole pieces are optional and are only used to increase the flux density in the magnetic fluid (if necessary) in order to increase sufficient pressure in the magnetic fluid.

A relief valve 36 which is provided in the downstream end of the flexible tubing 12 and a check valve 34 which is provided in the upstream end of said tubing 12 are utilized when the device 10 is operated in its pump mode. However, it should be appreciated that when the device 10 is operated in the control valve mode, these auxiliary valves 34 and 36 are not needed.

When operated in the control valve mode, the flexible tubing 12 of FIG. 1 is submersed and completely surrounded by the magnetic fluid 28 having a pressure somewhat in excess of the reservoir pressure. A strong magnetic field using the two permanent magnets 20 and 22 (only one permanent magnet may also be adequate for producing the magnetic field) creates an internal pressure in the magnetic fluid 28 which presses against the flexible tubing 12 and occludes it. The pole pieces 24 and 26 are provided to direct and concentrate the magnetic flux produced by the permanent magnets 20 and 22 at the point where the magnetic fluid 28 surrounds the flexible tubing 12. This occlusion therefore prevents any fluid flow through the tube 12. In non-human use, an electromagnet can be used in place of the permanent magnets.

To open this flexible tubing 12, a current is actuated from an external command signal (E.C.S.) and is directed along the coil 30 by suitable means such as described below. The current is controlled by a power transistor 40 which is powered by a standard rechargeable battery 42, e.g. a nickel cadmium battery. For minimum power consumption, the current can be a brief pulse as determined by a pulser 32 which controls the power transistor 40. The current generates a bucking magnetic field which counteracts the field from the permanent magnet and reduces the magnetic field in the magnetic fluid 28 and, therefore, reduces the pressure external to the tubing 12, allowing the liquid under internal pressure, i.e. within the tubing, to pass through the tubing 12 for the duration of the pulse.

The pulse creating this bucking magnetic field might typically be 0.3 amp for 10 milliseconds. However, once the pulse stops, the bucking magnetic field is terminated and the tube 12 is again occluded. Therefore, for a substantial amount of fluid to flow through the tube 12, there must be a plurality of these small pulses. Smaller current levels can be used if the coil has more turns. The required drive voltage is determined by the coil resistance which is reduced as the coil wire size is increased.

Alternatively, the fluid tube 12 can be opened by temporarily demagnetizing the permanent magnets 20 and 22 by a current pulse which is somewhat stronger than that required to merely buck out the permanent magnet field. The exact magnitude of this pulse is dependent upon the magnetic material which is employed as well as the length of that material, and this may be easily determined. To demagnetize these magnets, only one strong pulse is needed. When tube closure is desired, the permanent magnets can then be remagnetized by an oppositely directed current pulse. This remagnetizing pulse should be approximately five times stronger than the demagnetizing pulse. Although not shown in the drawing, the entire device 10, except for the discharge end of the tubing 12, is preferably enclosed in a housing which can be implanted into the body.

The device 10 can also be operated in the pump mode since the squeezing of the flexible tube by the application of a magnetic field thereto causes a tiny spurt of liquid to flow through the downstream end of the tube. In order to efficiently operate in this mode, however, a check valve 34 is provided between the reservoir 14 and the occluded variable sized portion of the passageway 12 to ensure that when the tube is occluded, the liquid flows toward the desired outlet in the body and not back to the reservoir 14.

The flow passage 12 passes within the magnetic field produced by the permanent magnets 20 and 22 and which can be neutralized by a briefly applied electromagnetic field. When the electromagnetic field is not present, the total field is large and the magnetic fluid is pressurized, collapsing the flow channel. When the electromagnetic field is present, the magnetic field from the permanent magnets 20 and 22 is cancelled so that the total field and the pressure in the magnetic field are small allowing the liquid from the reservoir to flow through the check valve 34 into the variable sized portion of the passageway 12 within the housing 16 and expand this portion of the passageway where it passes through the magnetic field. When the electromagnet field is turned off, the magnetic fluid pressure collapses this portion of the tubing 12 within the housing 16 and forces the liquid further along the flow passage, the check valve 34 preventing the liquid from returning to the reservoir.

The flow passage 12 connects to a normally closed outlet relief valve 36 which is overpowered by the pump pressure and allows the liquid flow displaced by the pump to pass through it. The relief valve prevents flow from the reservoir from passing through the system to the outlet while the variable sized portion of the passageway is filling. The relief valve 36 provides a fail-safe operation since it prevents uncontrolled delivery of the liquid if the electromagnet does not shut off allowing the low pressure reservoir to be connected to the outlet of the device. Furthermore, the system is also fail-safe in that if the current is not turned on due to a power failure, there is no pumping action and the relief valve 36 remains closed. The power consumption of this system will be low, since the check valve 34 and the relief valve 36 are both passive and since the magnetic fluid pump consumes only a brief pulse of power which need last only long enough for the pump to fill with the liquid.

Figure 2:
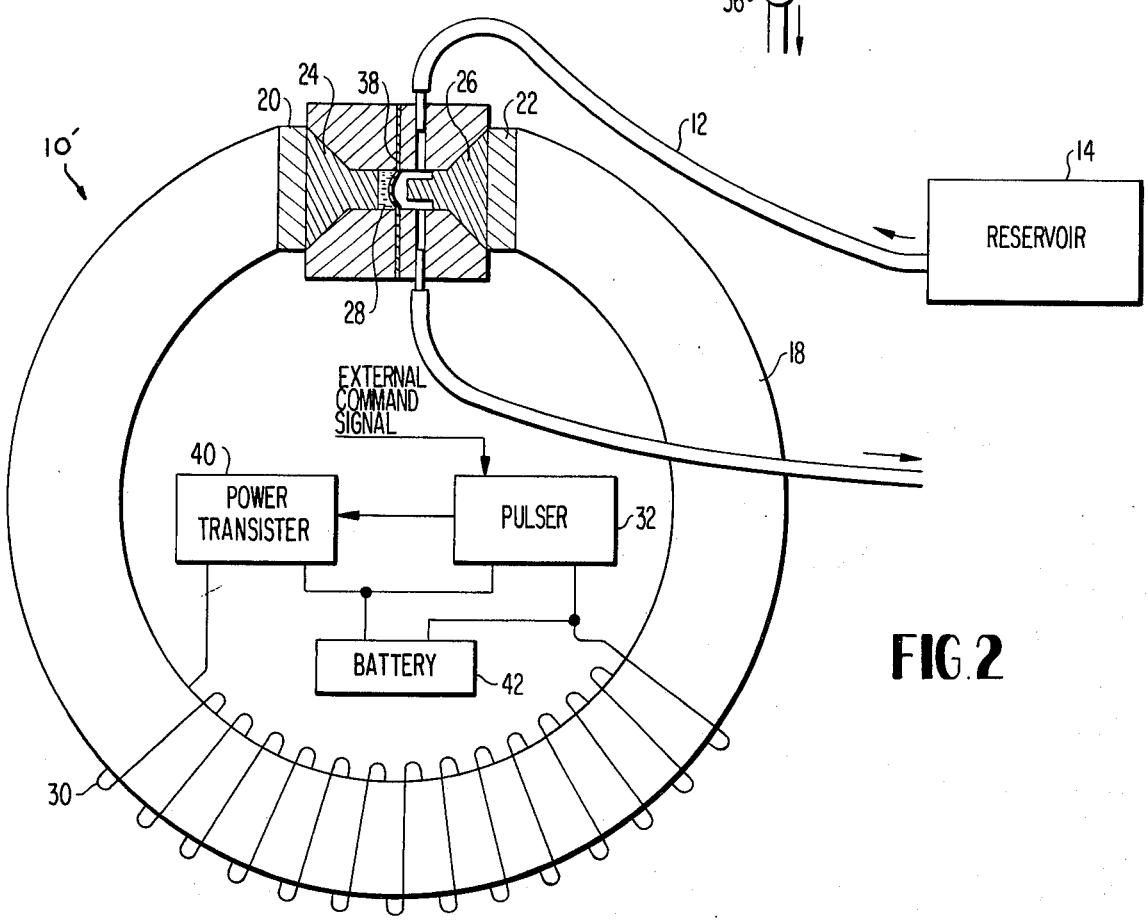
FIG. 2 is a schematic view of another embodiment of the electrically controlled magnetic fluid actuated switch in accordance with the present invention.

FIG. 2 shows an electrically controlled magnetic fluid actuated device 10' which contains an elastic membrane 38 as the variable sized portion of the passageway, the remaining elements being substantially the same as for the device 10. In the embodiment of FIG. 2, the magnetic fluid 28 is disposed on one side of the membrane 38 and the passageway is on the other side; therefore, in this embodiment it is not necessary to have the magnetic fluid surround the passageway. The liquid which is to be supplied to the body passes through the passageway on the other side of the membrane and, therefore, when the magnetic field of the permanent magnets is present as described above, the pressure of the magnetic fluid 28 forces the membrane 38 against the pole piece 26 thus occluding the flow passage. However, if the electromagnetic field is activated as indicated above to cancel the permanent magnetic field, then the pressure of the medicine or other liquid pushes the membrane 38 away from the pole piece 26 and allows flow of the medicine or the like to the desired organ of the body.

The embodiment of FIG. 2 of the basic mechanism is also well suited for operation in the pump mode described above when it is suitably connected to a check valve and a relief valve in the flow path in the manner shown in FIG. 1.

Either of the devices of FIGS. 1 or 2 may also be adapted for use in the relief valve mode, e.g. for use as a relief valve 36. In such a case the electrical components are not used, and the variable cross-section portion of the passageway passes between the pole pieces 24 and 26 of the permanent magnet without providing means to oppose or cancel the magnetic field of the permanent magnet. Thus, the magnetic fluid always tries to occlude the variable cross-section portion of the passageway, and whether or not the passageway opens depends on the magnitude of the upstream pressure. Accordingly, when the upstream pressure, e.g. in the reservoir 14, exceeds the external pressure exerted on the variable cross-section portion of the tubing 12 by the magnetic fluid, liquid passes through the tubing 12; otherwise the passageway remains closed.

While this device has been described with particular reference to its use in the body, it should not be construed to be so limited, and it may be utilized in many other situations. It will be obvious to those skilled in the art that various changes may be made without departing from the scope of the invention and the invention is not to be construed as limited to what is shown in the drawings and described in the specification. For example the toroidal iron core may be replaced with any suitable magnetically permeable material of any desired cross section and of such a shape as will complete the flux path between the two permanent magnets.

What is claimed is:

1. A magnetic fluid actuated relief valve for human implantation for controlling flow of liquid at pressures below a preselected value from an upstream position to a downstream position, comprising
    means to define a passageway having an upstream end and a downstream end, said passageway having an occludable portion of variable cross-section; and
    means to occlude said occludable portion of variable cross-section of said passageway, said means comprising a magnetic fluid in contact with the exterior of said occludable variable cross-section portion, and magnetizing means for providing a magnetic field of preselected magnitude for generating a preselected first pressure in said magnetic fluid sufficient to occlude said variable cross-section portion only when the upstream pressure in said passageway is below said preselected first value,
    whereby said relief valve opens against the force exerted by said first pressure of said magnetic fluid when the upstream pressure reaches a second pressure which exceeds said preselected first pressure.

2. A magnetic fluid actuated relief valve according to claim 1 wherein said magnetizing means comprises at least one permanent magnet.

3. A magnetic fluid actuated relief valve according to claim 2 wherein said magnetizing means comprises two said permanent magnets, each further having a flow concentrating pole piece connected thereto, said pole pieces directed toward said magnetic fluid.

4. A magnetic fluid actuated relief valve according to claim 2 wherein said passageway, including said variable cross-section portion, is a flexible tubing.

5. A magnetic fluid actuated relief valve according to claim 2 wherein said variable cross-section portion comprises a chamber having a flexible membrane wall, said magnetic fluid lying adjacent said membrane.

6. An electrically controlled magnetic fluid actuated control valve for human implantation for controlling flow of liquid from an upstream position to a downstream position comprises:
    means to define a passageway having an upstream end and a downstream end, said passageway having an occludable portion of variable cross-section;
    means to occlude said occludable portion of variable cross-section of said passageway, said means comprising a magnetic fluid in contact with the exterior of said variable cross-section portion, and magnetizing means for providing a magnetic field for generating a first pressure in said magnetic fluid sufficient to occlude said variable cross-section portion regardless of the pressure of upstream fluid in said passageway; and
    means to reduce the magnetic field to open said passageway, said means comprising demagnetizing means directed to said magnetizing means for reducing the magnetic field of said magnetizing means to reduce said internal magnetic fluid pressure and open said variable cross-section portion, and means to energize said demagnetizing means.

7. An electrically controlled magnetic valve according to claim 6 wherein said magnetizing means comprises at least one permanent magnet, and said demagnetizing means comprises a magnetically permeable core and a coil wound about said core.

8. A device in accordance with claim 7 wherein said magnetizing means comprises two said permanent magnets, each further having a flow concentrating pole pieces connected thereto, said pole pieces being directed toward said magnetic fluid.

9. A device in accordance with claim 6 wherein said passageway, including said variable cross-section portion, comprises a flexible tubing.

10. A device in accordance with claim 6 wherein said variable cross-section portion comprises a chamber having as one wall a flexible membrane, said magnetic fluid lying adjacent said membrane.

11. An electrically actuated pump for human implantation for controlling flow of liquid from an upstream position to a downstream position, comprising:
   a passageway having an upstream end and a downstream end, said passageway having a portion of variable cross-section intermediate said upstream end and said downstream end;
   a check valve upstream of said portion of variable cross-section, said check valve permitting the flow of liquid only in the downstream direction;
   means to occlude said portion of variable cross-section of said passageway, said means comprising a magnetic fluid in contact with the exterior of said variable cross-section portion, and magnetizing means for providing a magnetic field for generating an internal pressure in said magnetic fluid sufficient to occlude said variable cross-section portion;
   a relief valve along said passageway downstream of said variable cross-section portion, said relief valve having a predetermined set pressure less than the maximum magnetic fluid pressure;
   means to reduce the magnetic fluid to open said passageway at said variable cross-section portion; and
   control means to sequentially effect the application of external pressure by said magnetic fluid in contact with said variable cross-section portion through said magnetizing means to occlude said variable cross-section portion, and to thereafter energize said means to reduce the magnetic field to open said passageway at said variable cross-section portion so that said variable cross-section portion becomes filled with liquid but does not experience flow-through due to said relief valve, and thereafter to effect reapplication by said magnetic fluid of external pressure through said magnetizing means to occlude said variable cross-section portion and thereby force liquid through said relief valve to the point of delivery.

12. An electrically actuated pump according to claim 11 wherein said magnetizing means comprises at least one permanent magnet, and said demagnetizing means comprises a magnetically permeable core and a coil wound around said core.

13. An electrically actuated pump according to claim 12 wherein said magnetizing means comprises two said permanent magnets, each further having a flow concentrating pole piece connected thereto, said pole pieces directed toward said magnetic fluid.

14. An electrically actuated pump according to claim 11 wherein said passageway, including said variable cross-section portion, comprises a flexible tubing.

15. An electrically actuated pump according to claim 11 wherein said variable cross-section portion comprises a chamber having as one wall a flexible membrane, said magnetic fluid lying adjacent said membrane.

* * * * *